United States Patent
Demian

(10) Patent No.: US 7,383,089 B2
(45) Date of Patent: *Jun. 3, 2008

(54) BUNION TREATING DEVICE

(76) Inventor: Bassem M. Demian, 430 Shore Line Pl., Brick, NJ (US) 08723

( * ) Notice: Subject to any disclaimer, the term of this patent is extended or adjusted under 35 U.S.C. 154(b) by 562 days.

This patent is subject to a terminal disclaimer.

(21) Appl. No.: 10/870,221

(22) Filed: Jun. 17, 2004

(65) Prior Publication Data

US 2004/0243197 A1    Dec. 2, 2004

Related U.S. Application Data

(62) Division of application No. 09/716,567, filed on Nov. 20, 2000, now Pat. No. 6,862,481.

(51) Int. Cl.
*A61N 1/18* (2006.01)
(52) U.S. Cl. .......................... 607/72; 607/49; 607/115; 602/2
(58) Field of Classification Search .............. 607/72, 607/144, 49, 115; 602/2
See application file for complete search history.

(56) References Cited

U.S. PATENT DOCUMENTS

| | | |
|---|---|---|
| 2,827,049 A | 3/1958 | Scholl |
| 3,650,276 A | 3/1972 | Burghele et al. |
| 4,026,301 A | 5/1977 | Friedman et al. |
| 4,326,534 A | 4/1982 | Axelgaard et al. |
| 4,632,103 A | 12/1986 | Fabricant et al. |
| 4,729,369 A | 3/1988 | Cook |
| 4,930,504 A * | 6/1990 | Diamantopoulos et al. ... 607/88 |
| 4,940,046 A | 7/1990 | Jacoby |
| 5,094,226 A | 3/1992 | Medcalf et al. |
| 5,281,219 A | 1/1994 | Kallok |
| 5,578,065 A | 11/1996 | Hattori et al. |
| 5,674,267 A | 10/1997 | Mir et al. |
| 5,922,012 A | 7/1999 | Sakano |
| 6,341,237 B1 * | 1/2002 | Hurtado ...................... 607/148 |
| 6,456,884 B1 | 9/2002 | Kenney |

* cited by examiner

*Primary Examiner*—Carl H. Layno
*Assistant Examiner*—Eric D Bertram
(74) *Attorney, Agent, or Firm*—Carella, Bryne, Bain, et al.; John G. Gilfillan, III; William Squire

(57) ABSTRACT

A pulse generating apparatus has two like output channels that apply generated pulse signals of selected characteristics to two electrodes attached to a strap, each electrode receiving a different signal. The strap is attached to the foot so that the electrodes are positioned to stimulate with an electrical signal the abductor hallucis muscle of the foot to correct an imbalance due to overpowering by the adductor hallucis muscle. The signal strengthens the abductor hallucis muscle so that eventually it regains strength sufficient to counter balance the imbalance effect of the stronger adductor hallucis muscle and alleviate the bunion condition. The electrical signal generator generates signals that are pulses that are adjustable in frequency, modulation, pulse width and amplitude with modified square waves.

11 Claims, 5 Drawing Sheets

LOAD MODE: IM OHM
(OPEN CIRCUIT)
Ver. MODE: CH1
VOLT/DIV: 50.0V
TIME/DIV: 0.1MS

LOAD MODE: 500.00 OHM
VER. MODE: CH1
    TIME/DIV: 0.1MS
VOLT/DIV: 5.0V

BUNION TREATING DEVICE

This application is a divisional of U.S. application No. 09/716,567, filed Nov. 20, 2000, now U.S. Pat. No. 6,862,481

This invention relates to podiatric devices, and more particularly, to devices for the correction of bunion conditions in the foot.

U.S. Pat. No. 5,665,060 discloses a bunion treatment apparatus and method for minimizing the forces applied to a bunion and includes a planar main portion and a planar built-up portion constructed of flexible padding material. Strain relief cutouts are provided as well as a toe loop to prevent tearing of the main portion. This apparatus is provided merely to alleviate the discomfort of the condition rather than eliminating the condition.

U.S. Pat. No. 2,827,049 provides a bunion pad and suffers from a similar deficiency.

U.S. Pat. No. 4,729,369 discloses a toe splint and bunion correction device which attempts to correct the condition with a splint device which straightens the toe including a splint member and a Velcro fastener for securing the splint member to the foot. The splint member is plastic and is molded to accommodate the foot.

In U.S. Pat. No. 4,940,046 a pliable protector cushion pad device is disclosed for the big toe or hallux.

U.S. Pat. No. 4,632,103 shows a bandage to reduce bunion pain.

All of the above patents either try to minimize the pain of the bunion or use mechanical devices to correct the condition.

*Isoelectronic Rehabilitation Program—Advanced Clinical Applications-Podiatric Electrotherapy Applications* by Joe Kleinkort, 1989, 1992, is a manual that suggests electrotherapy applications for relaxation of muscle spasm, prevention or retardation of disuse atrophy, increasing local blood circulation, muscle reeducation, immediate postsurgical stimulation of calf muscles to prevent venous thrombosis and maintaining or increasing the range of motion. This manual discloses placement of electrodes to alleviate pain in various conditions in the ankle, feet and knee, and stimulation of muscles in cases of immobilization, An article entitled *Investigations on the origin of Hallux Valgus by Electromygraphic Analysis* by Takebe K. Shimazaki __1 Kobe J Medical Science 1981 August: 27(4): 139-58 discloses electromyographic analysis on the physiopathology of the Hallus Valgus and toes/physiopathology.

Stephen Guffey discloses, in a publication dated 1996, muscle reeducation employing electrical stimulation including frequencies, pulse duration, polarity, duty cycle, ramp, intensity, treatment time, how often, and electrode placement.

Electrode stimulation and muscle reeducation have generally been related to pain reduction. None of the above articles, however, relate to the problem of bunions and how to treat and correct the condition.

The present inventor recognizes that mechanical correction of the bunion condition is not satisfactory and a need is recognized for a more sophisticated device to correct the bunion condition. The pain reduction and muscle reeducation articles using electrotherapy have dealt primarily with leg and back problems or foot/ankle problems not associated with bunions. Present solutions for bunions is typically related to mechanical devices as disclosed in the aforementioned patents which approach correcting the problem with brute force mechanical splints and padding.

In contrast to the mechanical devices of the prior art to correction of bunion conditions in the foot, a method of correcting a bunion condition in a foot according to the present invention comprises the step of applying an electrical signal to the abductor hallucis muscle to strengthen the muscle to counter balance the strength of the adductor hallucis muscle.

In one aspect, the method includes means for applying repetitive cycles of electrical pulses to the abductor muscle.

In a further aspect, the pulses are modified square waves at a pulse repetition rate of 2 Hz to 150 Hz, a pulse width of about 60:s to 250:s.

The method in a further aspect includes cyclically increasing the pulse width.

In a further aspect, the method includes wrapping the foot and big toe of the foot with a corresponding strap, attaching at least one electrode to the strap with the electrode abutting the foot and then applying the electrical signal to the electrode.

The method in a fuirther aspect ftrther includes optimizing the signal to maximize said correction by adjusting the signal parameters until an optimum signal is generated. A bunion correction device according to the present invention comprises means for attaching at least one electrode to the foot for applying an electrical signal to the abductor hallucis muscle in the foot for strengthening the muscle to counter balance the strength of the foot adductor hallucis muscle and signal generator means for generating the electrical signal and applying the generated signal to the means for attaching.

In a still further aspect, the signal comprises a plurality of pulses and is settable in the range of 0-80 mA peak with either a positive or negative pulse into a 500 ohm load.

IN THE DRAWING

Figure 8:
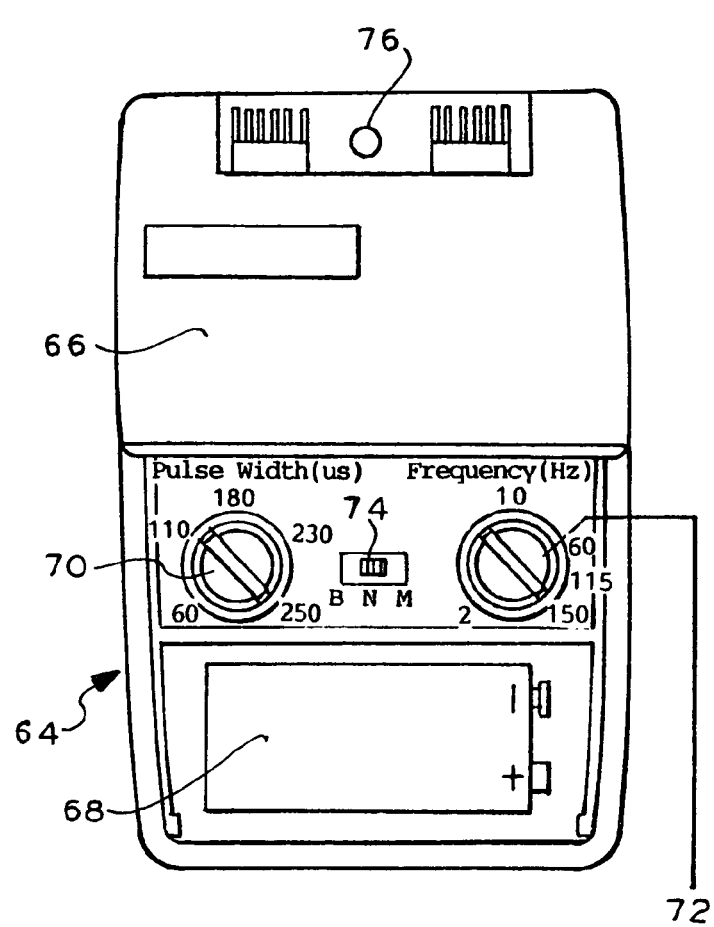
FIG. 8 is a front elevation view of an electrical signal generator for use with the device of FIGS. 5, 6 and 7.
Figure 10A:
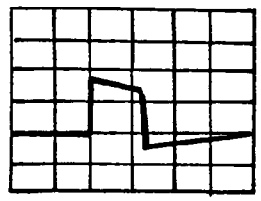
Figure 10B:
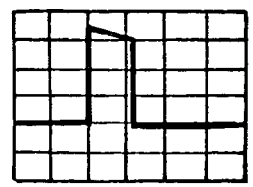
Figure 9:
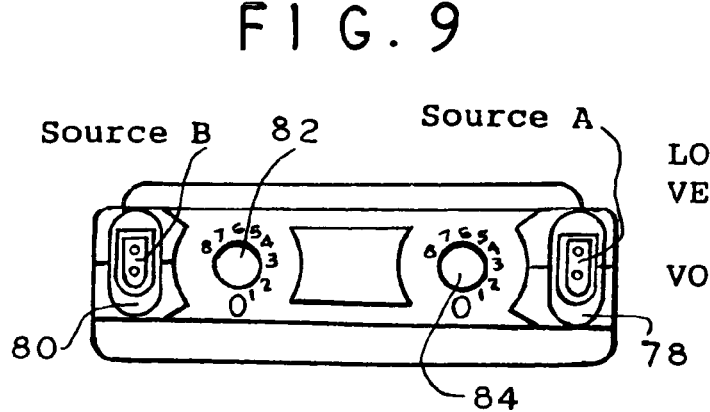
FIG. 9 is a top plan view of the generator of FIG. 8.
Figure 12A:
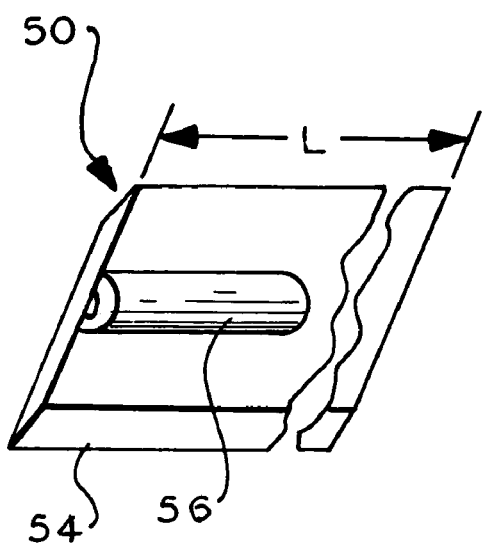
Figure 11:
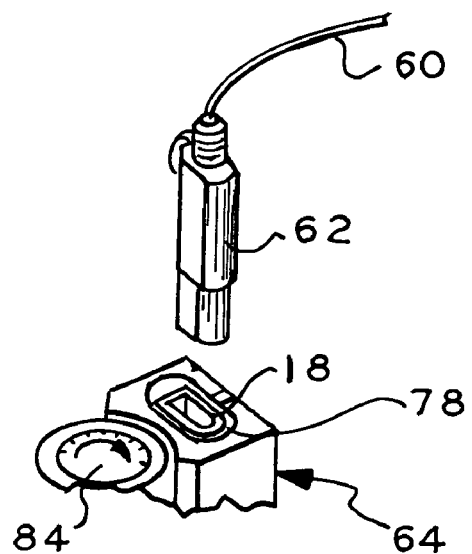
Figure 12:
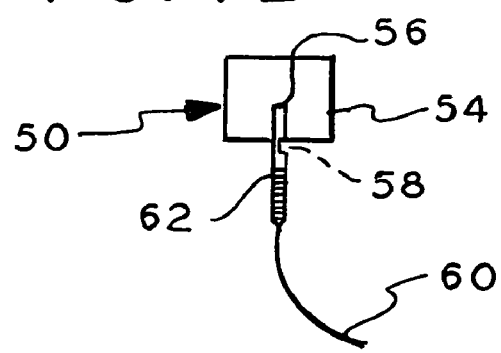

FIGS. 10*a* and 10*b* are waveform graphs of representative signals produced by the generator of FIG. 8;

FIG. 11 is an isometric view of a portion of the top of the generator of FIG. 9 showing the attachment of a the signal output cable of the generator to a representative output connector, there being two output connectors in the generator; and FIG. 12 is a top plan view of a representative electrode for applying a bunion correction signal to the foot; and FIG. 12*a* is an isometric view of the electrode of FIG. 12 without the electrical terminal in place.

Figure 1:
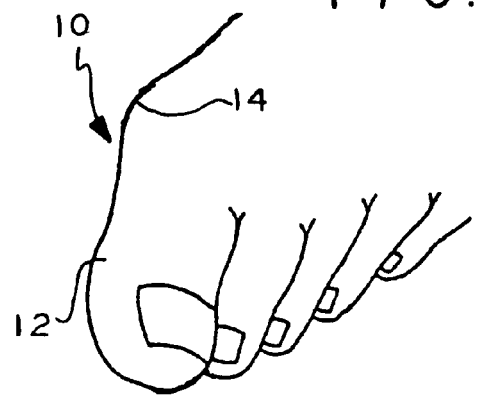
FIG. 1 is a perspective view of a foot exhibiting a bunion condition.
Figure 2:
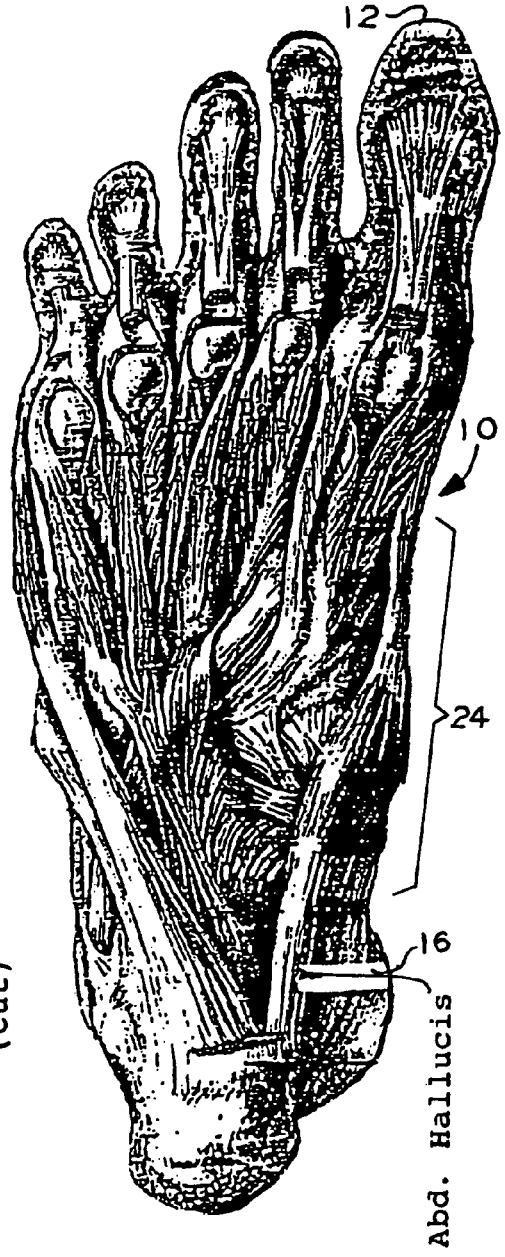
FIG. 2 is a top plan view of the anatomy of a foot showing the abductor hallucis muscle in the foot.
Figure 3:
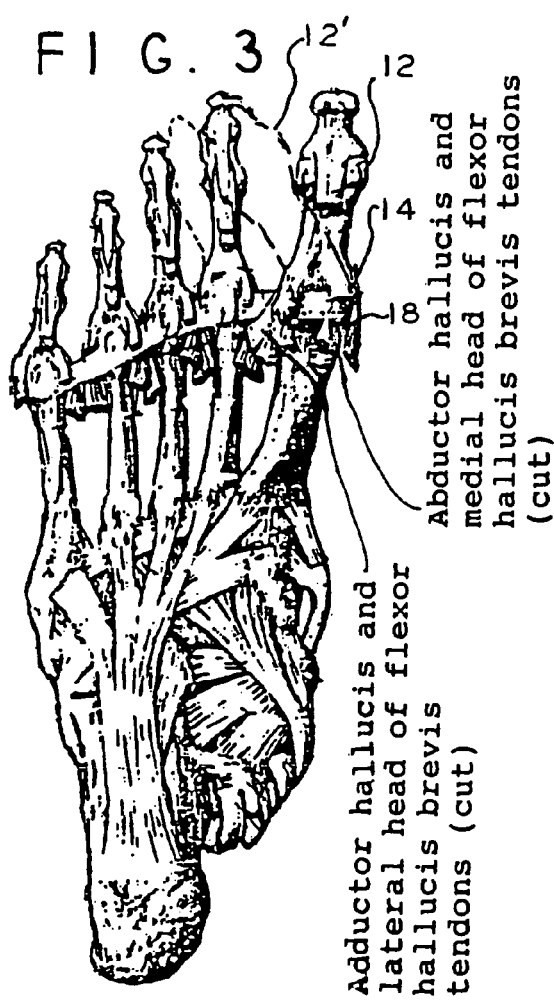
FIG. 3 is a top plan view of the anatomy of a foot showing the abductor hallucis and adductor muscles (cut away) in the foot which control the large toe.

In FIG. 1, foot 10 big toe 12 has a bunion 14. In FIG. 2 one muscle of the foot for controlling the big toe is the abductor hallucis muscle 16. In FIG. 3, a second muscle of the big toe is the adductor hallucis muscle 18 (shown cut away but in practice has an extent corresponding generally to the extent of the abductor hallucis muscle in FIG. 2. The present invention is a result of the recognition that the bunion 14 (shown in phantom in FIG. 3) is caused by the adductor hallucis muscle becoming stronger than the abductor hallucis muscle. Normally, in a healthy foot both muscles are of equal strength and counter balance the forces of each other in the normal quiescent state of the big toe.

However, over time due to mis-fitting shoes or due to genetic or disease problems, the strengths of the two muscles become different. The adductor muscle eventually overpowers the abductor muscle and pulls the big toe over to one side toward the other toes as shown in phantom in FIG. 3 by toe 12'. The abductor muscle 3 extends for the length of the foot as shown in FIG. 1 and is adjacent to both the side and top side surfaces of the foot.

It is known generally that muscles can be stimulated by electrical signals and this knowledge has been used to relieve pain due to muscle conditions, typically in the back, foot/ankle or leg. See the articles in the introductory portion. However, the present invention is a recognition that the bunion is due to a imbalance in the abductor and adductor hallucis muscles and that the abductor muscle can be strengthened by the application of electrical pulses thereto. The prior art has typically approached the correction of bunions with brute force by the use of mechanical devices and splints. The use of electrical signals to strengthen the abductor hallucis muscle corrects the problem by reducing the one sided impact imbalance of the stronger adductor hallucis muscle in persons exhibiting bunions.

Figure 4:
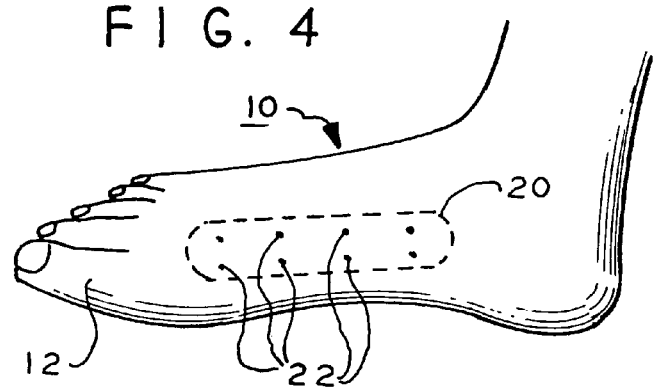
FIGS. 4 and 5 are respective similar side views of a foot which show generally the placement of electrodes for the correction of the bunion condition and a device according to an embodiment of the present invention employing electrodes for the correction of the bunion condition with electrical signals

In FIG. 4, foot 10 is shown with a region 20 in which the abductor hallucis muscle is located. One or more electrodes are placed in this region and an electrical signal applied to the electrodes to stimulate and repetitively relax and tighten the abductor hallucis muscle. The exact location can be determined empirically for each patient in order to ascertain the most optimum portion of the abductor hallucis muscle that is responsive to the electrical signal(s) for strengthening the muscle. This might take some trial and error until the optimum repositioning of the big toe 12 is observed. It is recommended that the major site of the abductor hallucis muscle be identified and the electrodes applied to this site. This site is believed to occur in the region 24, FIG. 2, in regard to the abductor hallucis muscle, which might vary of course from individual to individual.

Figure 5:
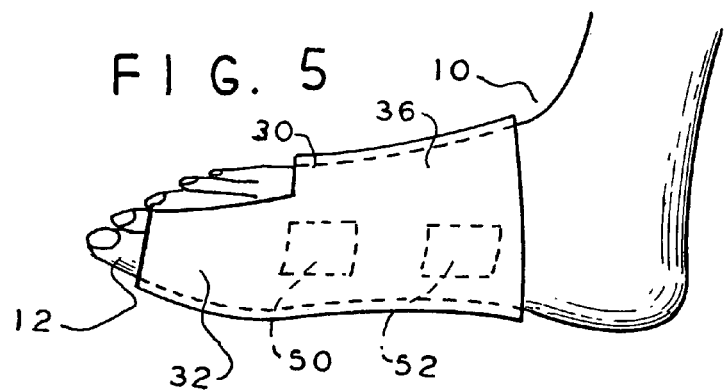
Figure 6:
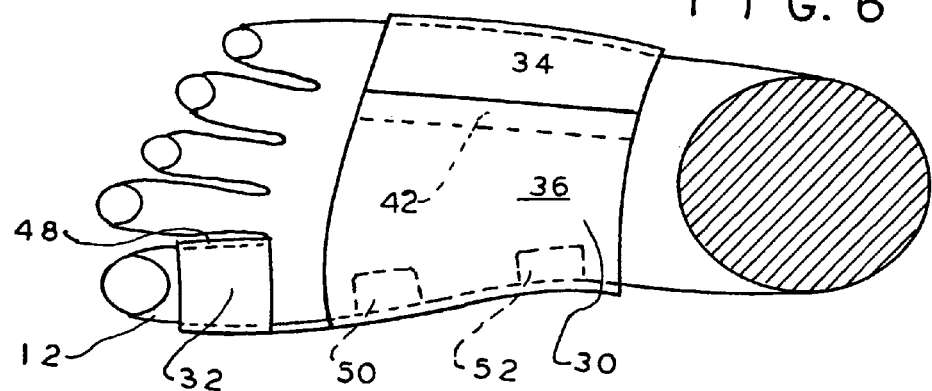
FIG. 6 is a plan view of the foot and device of FIG. 5.
Figure 7:
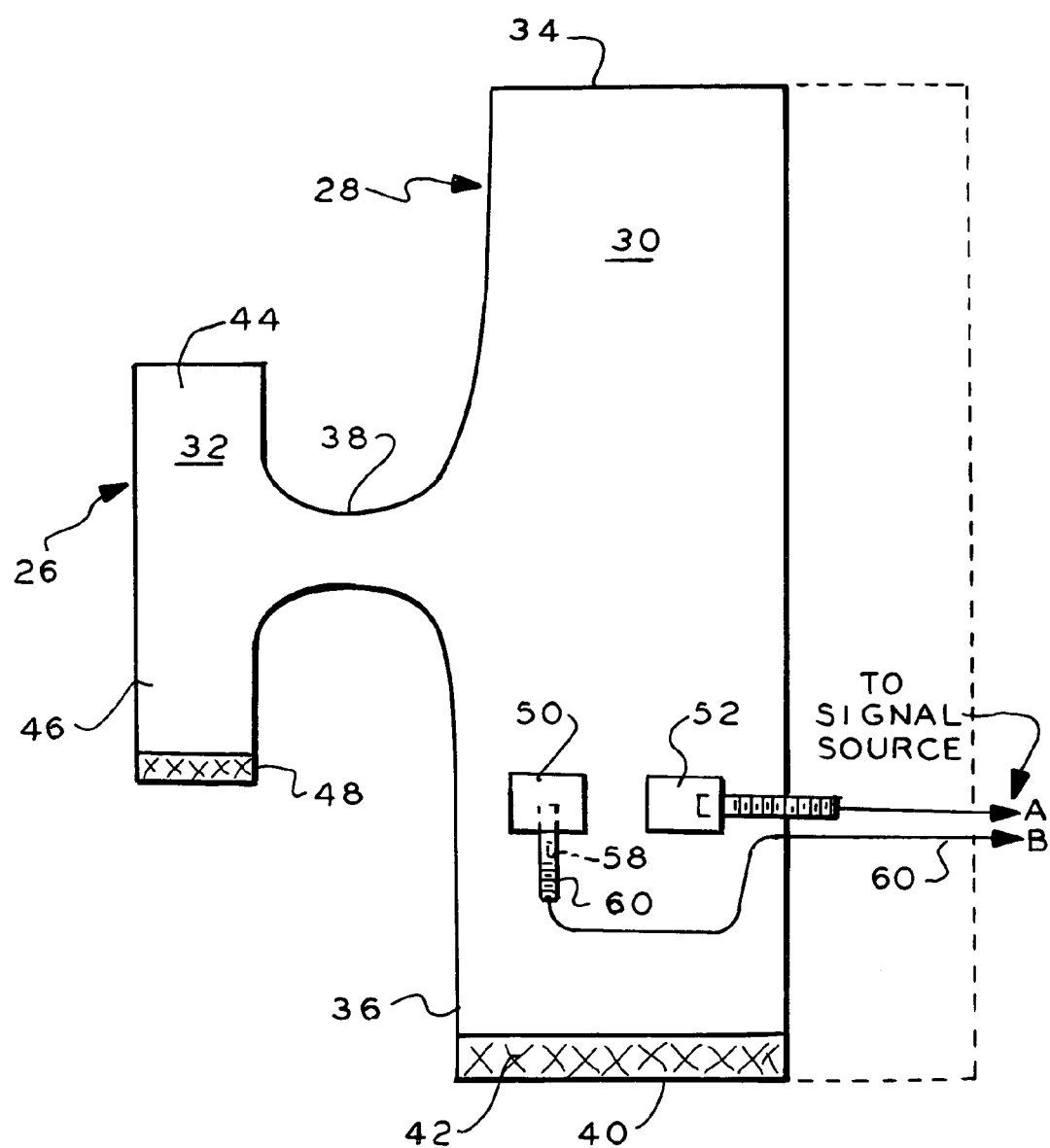
FIG. 7 is a plan view of the device of FIGS. 5 and 6 prior to attachment to a foot with representative electrodes attached for electrically correcting the bunion condition.

In FIG. 7, device 26 comprises a strap 28 formed of felt, foam or similar soft cushioning materials the composition of which is not important to the present invention other than it be electrical insulating material. Strap 28 comprises two substraps 30 and 32. Substrap 30 comprises a generally rectangular member with two opposing legs 34 and 36 of about the same width and attached one piece and integral with connecting member 38. Legs 34 and 36 are of like width from left to right in the figure. The end 40 of leg 36 has a strip 42 of Velcro hook members, a trademark for a hook and loop fastener well known and commercially available. The leg 34 and leg 36 overlap when wrapped about the foot as shown in FIGS. 5 and 6. The leg 36 strip 42 hooks engage the leg 34 which comprises loop type of fabric, or in the alternative, may include a strip (not shown) of Velcro loop material mating with the hook material strip 42. The hook and loop material releasably attach the overlapping two legs 34 and 36 of the substrap 30 as shown.

Substrap 32 comprises two legs 44 and 46 and Velcro hook strip 48. Legs 44 and 46 attach similarly as legs 34 and 36 about the big toe 12. Substrap 32 is connected to substrap 30 and integral one piece therewith by the connecting member 38. In FIG. 7, two electrodes 50 and 52 in this embodiment are attached to substrap 30 The electrodes 50 and 52 are identical and a description of electrode 50 is representative. In FIGS. 12 and 12a electrode 50 comprises a electrically conductive pad 54 which may be conductive elastomeric or plastic material. The pad 54 has a hollow somewhat tubular terminal connector 56 molded integral therewith. The pad 54 is square but may be other shapes. This electrode 50 is commercially available from the Lumiscope Company of Edison, N.J. as a kit with other components of the electrical signal generator to be described below as model SW1000 Transcutaneous Electrical Nerve Stimulator.

An electrical terminal 58 which is an elongated metal wire as typical in electrical connections and terminals, fits inside of the connector 56 to apply an electrical pulse signal to the pad 54. The pad 54 on a side opposite the connector 54 may receive an electrically conductive gel as known in this art for providing good electrical coupling to a local applied portion of the skin of the foot 10. An electrically conductive conductor 60 is connected to terminal 58 at one conductor end and to plug connector 62, FIG. 11, at the other conductor end.

In FIG. 8, electrical signal generator apparatus 64 has a housing 66 which receives a battery 68 (a conventional 9 volt transistor battery) with its electrical connection to the apparatus 64 and the housing cover not shown. The apparatus has a circuit which is commercially available (not shown and within the housing) and is available from the Lumiscope Company. Two control knobs 70 and 72 control the respective pulse width and frequency of the alternating current signal produced by the apparatus 64. A mode selector switch 74 selects burst (B), normal (N) and modulation (M) modes of the generated pulses. A power indicator light 76 is included. In FIG. 9, channel output receptacles 78 and 80 provide two parallel identical output signals generated by the apparatus 64. Knob 82 controls channel on/off state for receptacle 80 and the output signal amplitude for this receptacle. Knob 84 controls channel on/off state for receptacle 78 and the output signal amplitude for this receptacle.

The circuit of apparatus 64 provides dual identical channels which are electrically isolated. The circuit is a pulse generator for generating approximate adjustable square waves as shown in FIGS. 10a and 10b which are self explanatory. The amplitude of each channel is independently controlled, but otherwise the parameters of the signals of the two channels is the same as controlled by knobs 70 and 72 and mode select switch 74. The pulse amplitude is adjustable by knobs 82 and 84 in a range of 0-80 mA peak either with a positive pulse or negative pulse into a 500 ohm load for each channel. The pulse frequency is adjustable in the range of 2 Hz to 150 Hz. The pulse width is adjustable in the range of about 60:s to 250:s.

The apparatus has a modulation mode. The modulation mode is one where the pulse width is automatically varied in a cyclic pattern over an interval of nominally 4.0 seconds. The pulse width decreases linearly over a period of 1.0 seconds from the control setting value to a value which is decreased 40% maximum. The narrow pulse width will continue for 1.5 seconds maximum, then increase linearly over a 1.5 second period to its original value. The cycle is then repeated.

The apparatus also has a burst mode in which bursts of seven pulses are provided at a maximum pulse rate. The bursts occur twice a second.

The wave form as shown in FIGS. 10a and 10b are modified square waves with zero net direct current (DC) component. All of the adjustable parameters are set at the midpoint of the specified range. The apparatus has a voltage of 0-110 volts maximum either positive or negative pulse (open circuit). There is a maximum charge per pulse of 16 micro coulombs. The values may vary in a range of +/−20%. This apparatus is normally commercially available for treatment only of pain, chronic or adjunct to management of post surgical and post traumatic acute pain problems. However, as disclosed herein it may also be used to correct bunion conditions. The apparatus is available with the restriction that transcutaneous electrical nerve stimulation is of no known curative value other than pain relief.

The connector 62 is mated in receptacle 78, FIG. 11 to connect the electrode 50 to the output signal. The electrodes 50 an d52, FIG. 7, are bonded by a Velcro fastener to the strap 28, FIG. 7, leg 36. The location of the electrodes is determined for a given patient and determined on a case by case basis. The signal parameters are varied until optimum correction of the bunion is noted. This requires setting of the pulse parameters by the user during the initial set up. The user will note various nerve reactions to the electrical signals and by observation can determine optimum electrical impulses. The various parameters of the pulses are set to optimize the visual and physical results. While the particular electrical signal parameters are given herein, they are given by way of example, and not limitation. Other electrical signals of pulses of different shapes, currents, amplitudes and wave forms may also be used according to a given condition being corrected. Also, the shape and material of the strap is by way of example and not limitation. Other devices for applying the electrical signals may be utilized the device described herein being given by example only. The important aspect is that the abductor muscle is strengthened sufficiently so that the forces on the big toe muscles balance. The big toe thus returns to its normal position in response to the treatment described herein.

It will occur to one of ordinary skill that modifications may be made to the disclosed embodiments without departing from the scope of the invention as defined in the appended claims. The disclosed embodiments are given by way of illustration and not limitation. For example, while the foot muscles for the big toe involving a bunion condition are corrected herein, other muscles involving other limb distortions due to muscle imbalance may also be corrected by applying electrical signals to strengthen certain of such other muscles.

What is claimed is:

1. A bunion correction device comprising:
   a strap comprising a first strap for encircling the big toe and a second strap for encircling the foot;
   at least one electrode attached to the strap;
   the strap being arranged for attaching the at least one electrode to the foot aligned with the abductor hallucis muscle of the foot, the electrode for applying an electrical signal to the abductor hallucis muscle to counter balance the strength of the foot adductor hallucis muscle to thereby correct a bunion condition in the foot; and
   a signal generator for generating the electrical signal and applying the generated signal to the at least one electrode.

2. The device of claim 1, wherein the first and second straps cooperate for aligning the at least one electrode to the abductor hallucis muscle in the foot.

3. The device of claim 2 wherein the at least one electrode includes two spaced electrodes on the strap for overlying the abductor hallucis muscle of the foot in two spaced locations.

4. The device of claim 1 wherein the signal generator includes an arrangement for applying a generated signal to two electrodes.

5. The device of claim 4 wherein the signal generator includes a circuit for generating two signals and applying a different signal of the two signals to each electrode.

6. The device of claim 1 wherein the signal generator includes a circuit for generating a plurality of pulses and includes an arrangement for setting the pulses in the range of 0-80 mA peak with either a positive or negative pulse into a 500 ohm load.

7. The device of claim 6 wherein the signal generator includes a circuit for generating bursts of pulses of about 7 pulses at a maximum pulse rate and an arrangement for setting the pulses in the range of 0-80 mA peak with either a positive or negative pulse into a 500 ohm load.

8. The device of claim 1 wherein the signal generator includes a circuit for generating a plurality of pulses at a frequency in the range of about 2 Hz to 150 Hz and an arrangement for setting the pulses in the range of 0-80 mA peak with either a positive or negative pulse into a 500 ohm load.

9. The device of claim 1 wherein the signal generator includes a circuit for generating a plurality of pulses with a pulse width in the range of about 60:s to 250:s and an arrangement for setting the pulses in the range of 0-80 mA peak with either a positive or negative pulse into a 500 ohm load.

10. The device of claim 1 the signal generator is for generating a plurality of pulses and an includes arrangement for setting the pulses in the range of 0-80 mA peak with either a positive or negative pulse into a 500 ohm load, the generator for generating bursts of pulses twice a second.

11. A bunion correction device comprising:
    a connection arrangement for attaching at least one electrode to the foot, the at least one electrode for applying an electrical signal to the abductor hallucis muscle in the foot, the electrical signal for strengthening the muscle to counter balance the strength of the foot add uctor hallucis muscle, the connection arrangement comprising a strap having interconnected first and second substraps, the first substrap for being attached solely to the big toe and the second substrap for being attached to the foot solely between the toes and ankle, the at least one electrode being coupled to the second substrap, the first and second straps being dimensioned to align the at least one electrode with the abductor hallucis muscle; and
    a signal generator for generating the electrical signal and applying the generated signal to the at least one electrode to correct the bunion condition.

* * * * *